US012589189B2

(12) United States Patent
Susen et al.

(10) Patent No.: US 12,589,189 B2
(45) Date of Patent: Mar. 31, 2026

(54) USE OF RETINOIC ACID RECEPTOR (RAR) AGONISTS FOR REVERSING, PREVENTING, OR DELAYING CALCIFICATION OF AORTIC VALVE

(71) Applicants: INSERM (Institut National de la Santé et de la Recherche Médicale), Paris (FR); Université de Lille, Lille (FR); Institut Pasteur de Lille, Lille (FR); Centre Hospitalier Régional Universitaire de Lille, Lille (FR)

(72) Inventors: Sophie Susen, Lille (FR); Delphine Corseaux, Lille (FR); Yoann Sottejeau, Lille (FR); Mickael Rosa, Lille (FR); Jérôme Soquet, Lille (FR); Eric Van Belle, Lille (FR); Bart Staels, Lille (FR); Annabelle Dupont, Lille (FR)

(73) Assignees: INSERM (INSTITUTE NATIONAL DE LA SANTA ET DE LA RECHERCHE MEDICALE), Paris (FR); Université de Lille, Lille (FR); Instiut Pasteur de Lille, Lille (FR); Centre Hospitalier Régional Universitaire de Lille, Lille (FR)

( * ) Notice: Subject to any disclaimer, the term of this patent is extended or adjusted under 35 U.S.C. 154(b) by 948 days.

(21) Appl. No.: 17/760,568

(22) PCT Filed: Oct. 1, 2020

(86) PCT No.: PCT/EP2020/077456
§ 371 (c)(1),
(2) Date: Mar. 15, 2022

(87) PCT Pub. No.: WO2021/064072
PCT Pub. Date: Apr. 8, 2021

(65) Prior Publication Data
US 2022/0339322 A1 Oct. 27, 2022

(30) Foreign Application Priority Data
Oct. 2, 2019 (EP) .................................... 19306256

(51) Int. Cl.
A61L 27/54 (2006.01)
A61K 31/196 (2006.01)
A61K 31/203 (2006.01)
A61L 27/18 (2006.01)

(52) U.S. Cl.
CPC ............ *A61L 27/54* (2013.01); *A61K 31/196* (2013.01); *A61K 31/203* (2013.01); *A61L 27/18* (2013.01); *A61L 2300/21* (2013.01); *A61L 2400/02* (2013.01); *A61L 2430/20* (2013.01)

(58) Field of Classification Search
CPC ... A61K 31/192; A61K 31/196; A61K 31/203
See application file for complete search history.

(56) References Cited

PUBLICATIONS

Perone, Eur Soc. Of Cardiology, 2020 (Year: 2020).*
Penn Medicine, https://www.pennmedicine.org/conditions/aortic-valve-stenosis, 2025 (Year: 2025).*
UCLA Health, 2025 (Year: 2025).*
Focused Ultrasound foundation (https://www.fusfoundation. org/diseases-and-conditions/heart-valve-calcifications/, 2025 (Year: 2025).*
Arterioscler Thromb Vasc Biol. Author manuscript; available in PMC 2021 (Year: 2021).*
Lindman, Clin Res, PMC, 2014 (Year: 2014).*
Huk et al, "Increased Dietary intake of Vitamin A promotes Valve Calcification in Vivo.", Arterioscler. Thromb Vasc. Biol, vol. 33, p. 285-293, 2012.
Takeda Norifumi; Manabe Ichiro; Shindo Takayuki; Iwata Hiroshi; Iimuro Satoshi; Kagechika Hiroyuki; Shudo Koichi; Nagai Ryozo, "Synthetic retinoid Am80 reduces scavenger receptor expression and atherosclerosis in mice by inhibiting IL-6.", Arteriosclerosis, Thrombosis, and Vascular Biology,vol. 26, No. q, p. 1177-1183, 2006.
Peacock Jacqueline D; Levay Agata K; Gillaspie Devin B; Tao Ge; Lincoln Joy, "Reduced sox9 function promotes heart valve calcification phenotypes in vivo", Circulation Research, vol. 106, p. 712-719, 2010.

* cited by examiner

*Primary Examiner* — Umamaheswari Ramachandran
(74) *Attorney, Agent, or Firm* — WCF IP

(57) ABSTRACT

Aortic valve calcification is a condition in which calcium deposits form on the aortic valve in the heart. These deposits can cause narrowing at the opening of the aortic valve. This narrowing can become severe enough to reduce blood flow through the aortic valve—a condition called aortic valve stenosis. The inventors have shown that retinoic acid decreases calcification and osteoblast-like phenotype in valvular interstitial cells (VICs). More particularly, RARα activation reduces calcification and osteoblast-like phenotype in VIC. On the contrary, ALDH1A1 inhibition increases calcification and osteoblast-like phenotype in VIC. Thus the results prompt to consider that use or retinoic acid receptor (RAR) agonists would be suitable for the reversing, preventing or delaying calcification of the aortic valve.

6 Claims, 5 Drawing Sheets

Figure 1A:
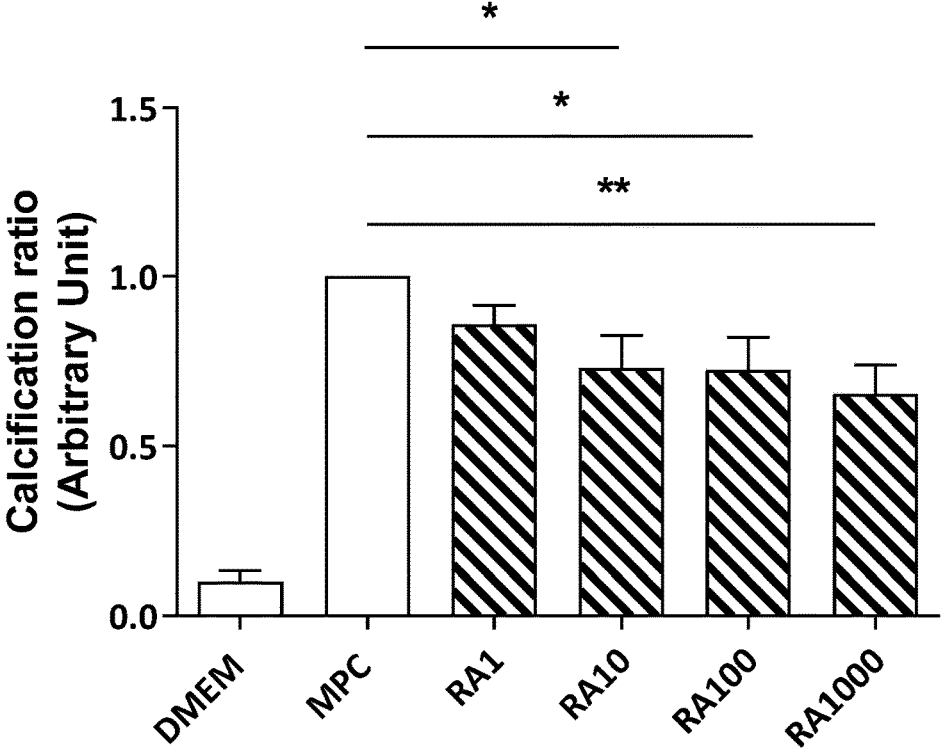

USE OF RETINOIC ACID RECEPTOR (RAR) AGONISTS FOR REVERSING, PREVENTING, OR DELAYING CALCIFICATION OF AORTIC VALVE

FIELD OF THE INVENTION

The present invention is in the field of medicine and in particular in cardiology.

BACKGROUND OF THE INVENTION

Aortic valve calcification is a condition in which calcium deposits form on the aortic valve in the heart. These deposits can cause narrowing at the opening of the aortic valve. This narrowing can become severe enough to reduce blood flow through the aortic valve—a condition called aortic valve stenosis.

In particular, calcific aortic valve disease (CAVD) is the most common valvular heart disease in adults, affecting 2-6% of people over 65 years [1]. First described as a passive, degenerative process related to repetitive high mechanical stress, it is now clear that CAVD is an atherosclerosis-like disease mediated by lipid deposition, inflammation, fibrosis and calcification [2, 3]. The symptoms of CAVD vary depending on the degree of valve stenosis. Patients with mild to moderate CAVD may lack symptoms as symptoms typically appear in those patients with severe CAVD. Symptoms can include progressive shortness of breath on exertion, syncope, chest pain, and sudden death. Effective treatments are represented by valve replacement either by transcatheter aortic valve implantation (TAVI) or by surgical aortic valve replacement. In recent time, the use of bioprosthetic valves (BPVs) vs mechanic valves for treating AVS with TAVI has considerably increased. The primary cause of long-term failure of BPV is structural valve deterioration due to tissue calcification. Recent studies have reported similarities between histological findings in stenosed AV and explanted degenerated BPV. So far, no targeted medical therapy is proven to prevent, slow down or treat fibrocalcific AVS or to prevent BPV degeneration.

Valvular interstitial cells (VICs) are the most prevalent cells found in human aortic valves and play a major role in tissue homeostasis and valve function [4]. These cells represent a heterogeneous and dynamic cell population composed of progenitor cells, quiescent cells, activated cells and osteoblast-like cells [5]. Recent studies have suggested that this latter cell phenotype plays an important role in valve calcification, a hallmark of CAVD [3, 6]. A better understanding of VIC biology, major component of aortic valve and effectors of valve fibrocalcification, may provide therapeutic targets for prevent, slow or stop fibrocalcification progression. Retinoic pathway has documented effects on inflammatory, fibrotic, angiogenesis and calcifying processes in other cells that VIC. For example, retinoid acid, the bioactive metabolic of vitamin A, inhibits osteoblastic mineralization (Lind, 2013) and reduces the expression of osteoprotegerin through activation of retinoid acid receptors in osteoblasts (Jacobson, 2004). Interestingly, retinoid acid is a negative regulator of osteoblast differentiation and inhibits calcifications in mesenchymal progenitor cells which have same properties than VIC to differentiate (Green, 2017). Today there are few data on the role of retinoids and associated nuclear receptors on CAVD. To our knowledge, the only published experimental data on the potential role of retinoids on aortic valve calcification suggests that an excess of vitamin A dietary intake could promote heart valve calcification (Huk D J, Hammond H L, Kegechika H, Lincoln J. Increased dietary intake of vitamin A promotes aortic valve calcification in vivo. Arterioscler Thromb Vasc Biol. 2013 February; 33(2):285-93).

SUMMARY OF THE INVENTION

As defined by the claims, the present invention relates to the use of retinoic acid receptor (RAR) agonists for reversing, preventing, or delaying calcification of aortic valve.

DETAILED DESCRIPTION OF THE INVENTION

The first object of the present invention relates to a method of reversing, preventing, or delaying calcification of aortic valve in a patient in need thereof comprising administering to the patient a therapeutically effective amount of a retinoic acid receptor (RAR) agonist.

As used herein, the term "valve" may refer to the valve that prevent the backflow of blood during the rhythmic contractions. There are four main heart valves. In particular, the aortic valve separates the left ventricle and aorta. The term "aortic valve" includes a diseased aortic valve or a bioprosthetic valve.

As used herein, the term "bioprosthetic valve" is a stented tissue heart valve and may refer to a device used to replace or supplement an aortic valve that is defective, malfunctioning, or missing. Examples of bioprosthetic valve prostheses include, but are not limited to, TS 3fs® Aortic Bioprosthesis, Carpentier-Edwards PERIMOUNT Magna Ease Aortic Heart Valve, Carpentier-Edwards PERIMOUNT Magna Aortic Heart Valve, Carpentier-Edwards PERIMOUNT Magna Mitral Heart Valve, Carpentier-Edwards PERIMOUNT Aortic Heart Valve, Carpentier-Edwards PERIMOUNT Plus Mitral Heart Valve, Carpentier-Edwards PERIMOUNT Theon Aortic Heart Valve, Carpentier-Edwards PERIMOUNT Theon Mitral Replacement System, Carpentier-Edwards Aortic Porcine Bioprosthesis, Carpentier-Edwards Duraflex Low Pressure Porcine Mitral Bioprosthesis, Carpentier-Edwards Duraflex mitral bioprosthesis (porcine), Carpentier-Edwards Mitral Porcine Bioprosthesis, Carpentier-Edwards S.A.V. Aortic Porcine Bioprosthesis, Edwards Prima Plus Stentless Bioprosthesis, Edwards Sapien Transcatheter Heart Valve, Medtronic, Freestyle® Aortic Root Bioprosthesis, Hancock® II Stented Bioprosthesis, Hancock II Ultra® Bioprosthesis, Mosaic® Bioprosthesic, Mosaic Ultra® Bioprosthesis, St. Jude Medical, Biocor®, Biocor™ Supra, Biocor® Pericardia, Biocor™ Stentless, Epic™, Epic Supra™, Toronto Stentless Porcine Valve (SPV®), Toronto SPV II®, Trifecta, Sorin Group, Mitroflow Aortic Pericardial Valve®, Cryolife, Cryolife aortic Valve® Cryolife pulmonic Valve®, Cryolife-O'Brien stentless aortic xenograft Valve® and all variations thereof. Generally, bioprosthetic valve comprise a tissue valve having one or more cusps and the valve is mounted on a frame or stent, both of which are typically elastical. As used herein, the term "elastical" means that the device is capable of flexing, collapsing, expanding, or a combination thereof. The cusps of the valve are generally made from tissue of mammals such as, without limitation, pigs (porcine), cows (bovine), horses, sheep, goats, monkeys, and humans.

As used herein, the expression "calcification of the aortic valve" has its general meaning in the art and refers to formation, growth or deposition of extracellular matrix hydroxyapatite (calcium phosphate) crystal deposits in the aortic valve, including a bioprosthetic valve.

In some embodiments, the method of the present invention is particularly suitable for primary prevention of calcification. In particular, the method of the present invention is suitable for the treatment of calcific aortic valve disease. As used herein, the term "calcific aortic valve disease" or "CAVD" has its general meaning in the art and refers to a slowly progressive disorder with a disease continuum that ranges from mild valve thickening without obstruction of blood flow, termed aortic sclerosis, to severe calcification with impaired leaflet motion, or aortic stenosis. Thus disease progression is generally characterized by a process of thickening of the valve leaflets and the formation of calcium nodules—often including the formation of actual bone—and new blood vessels, which are concentrated near the aortic surface. End-stage disease, e.g., calcific aortic stenosis, is generally characterized pathologically by large nodular calcific masses within the aortic cusps that protrude along the aortic surface into the sinuses of Valsalva, interfering with opening of the cusps. In some embodiments, the method of the present invention is particularly suitable for the treatment of calcific aortic stenosis.

In some embodiments, the method of the present invention is particularly suitable for secondary prevention of calcification. In particular, the method of the present invention is particularly suitable for preventing degeneration of an implanted bioprosthetic valve. Thus in some embodiment, the method of the present invention is particularly suitable for delaying or preventing the calcification of a bioprosthetic valve after valve replacement either surgically or after transcatheter aortic valve implantation (TAVI).

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some aspects, the method of the present invention is particularly suitable for preventing stenosis. As used herein, the term "stenosis" refers to the narrowing of the aortic valve that could block or obstruct blood flow from the heart and cause a back-up of flow and pressure in the heart.

As used herein, the term "retinoic acid receptor" or "RAR" has its general meaning in the art and refers to a type of nuclear receptor which can also act as a transcription factor that is activated by both all-trans retinoic acid and 9-cis retinoic acid. There are three retinoic acid receptors (RAR), RARα, RARβ and RARγ, encoded by the RARA, RARB, RARG genes, respectively. Each receptor isoform has ten splice variants: four for alpha, four for beta, and two for gamma. RAR receptors activate transcription by binding to DNA sequence elements, known as RAR response elements (RARE), in the form of a heterodimer with retinoid X receptors (known as RXRs).

As used herein, the term "retinoic acid receptor (RAR) agonist" is intended to mean those compounds recognized in the art as those capable of acting through retinoic acid receptors and are efficient at inducing RARE-dependent gene expression. Preferably, the RAR agonist is a RARα agonist. The prior art contains a large number of chemical compounds that are RAR agonists. Among the prior art documents, mention may, for example, be made of patent EP 0 816 352 B1 which describes aromatic biaryl heterocyclic compounds for the treatment of dermatological, rheumatic, respiratory and opthalmological conditions, but also for cosmetic uses, document WO 2005/056510 which describes molecules comprising an aromatic ring substituted with a hydroxyalkyl radical, documents WO 99/10308 and WO 2006/066978 which describe substituted biphenyl derivatives, documents U.S. Pat. No. 6,218,128 and EP 0879814 which describe bicyclic and/or tricyclic compounds, document EP 0850909 which describes stilbene compounds, document WO 98/56783 which describes biaromatic compounds, and documents EP 0776885 and EP 0776881 which describe biaromatic compounds comprising adamantyl groups. The RAR agonist selectivity of a compound can be determined by routine ligand binding assays known to one of skill in the art such as described in C. Apfel et al., Proc. Nat. Sci. Acad. (USA), 89: 7129-7133 (1992); M. Teng et al., J. Med. Chem., 40: 2445-2451 (1997); and PCT Publication WO 96/30009. For instance known RARα agonists include but are not limited to: TTNPB, tamibarotene, 9-cis-retinoic acid, trans-retinoic acid, AGN193836, Ro 40-6055, CD666, and BMS753. In some embodiments, the RARα agonist is 4-[[(5,6,7,8-Tetrahydro-5,5,8,8-tetramethyl-2-naphthalenyl)amino]carbonyl]benzoic acid (AM80).

By a "therapeutically effective amount" is meant a sufficient amount of the agonist of the present invention for the treatment of the aortic valve stenosis at a reasonable benefit/risk ratio applicable to any medical treatment. It will be understood that the total daily usage of the compound will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically, the agonist of the present invention may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. The agonist of the present invention can be formulated into a composition in a neutral or salt form. Pharmaceutically acceptable salts include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils.

The present invention also relates to the use of a RAR agonist of the present invention for the preparation of bioprosthetic valve. In this respect, the invention relates more particularly to bioprosthetic valve comprising an amount of a RAR agonist. Such a local biomaterial or medical delivery device can be used to treat aortic valve stenosis. Such biomaterial or medical delivery device may be biodegradable. The agonist of the invention is preferably entrapped into the cusps of the valve. The cusps of the valve are generally made from tissue of mammals such as, without limitation, pigs (porcine), cows (bovine), horses, sheep, goats, monkeys, and humans. With said entrapment, it is possible to achieve a high level of local action. According to the present invention, the valve may be a collapsible elastical valve having one or more cusps and the collapsible elastical valve may be mounted on an elastical stent. In some embodiments, the collapsible elastical valve may comprise one or more cusps of biological origin. In some embodiments, the one or more cusps are porcine, bovine, or human. The elastical stent portion of the valve prosthesis used in the present invention may be self-expandable or expandable by way of a balloon catheter. The elastical stent may comprise any biocompatible material known to those of ordinary skill in the art. Examples of biocompatible materials include, but are not limited to, ceramics; polymers; stainless steel; titanium; nickel-titanium alloy, such as nitinol; tantalum; alloys containing cobalt, such as Elgiloy® and Phynox®; and the like. The process of disposing the coating composition which comprises the RAR agonist of the present invention may be any process known in the art. The local delivery according to the present invention allows for high concentration of the agonist of the present invention at the disease site with low concentration of circulating compound. For purposes of the invention, a therapeutically effective amount will be administered.

The invention will be further illustrated by the following figures and examples. However, these examples and figures should not be interpreted in any way as limiting the scope of the present invention.

FIGURES

Figure 1B:
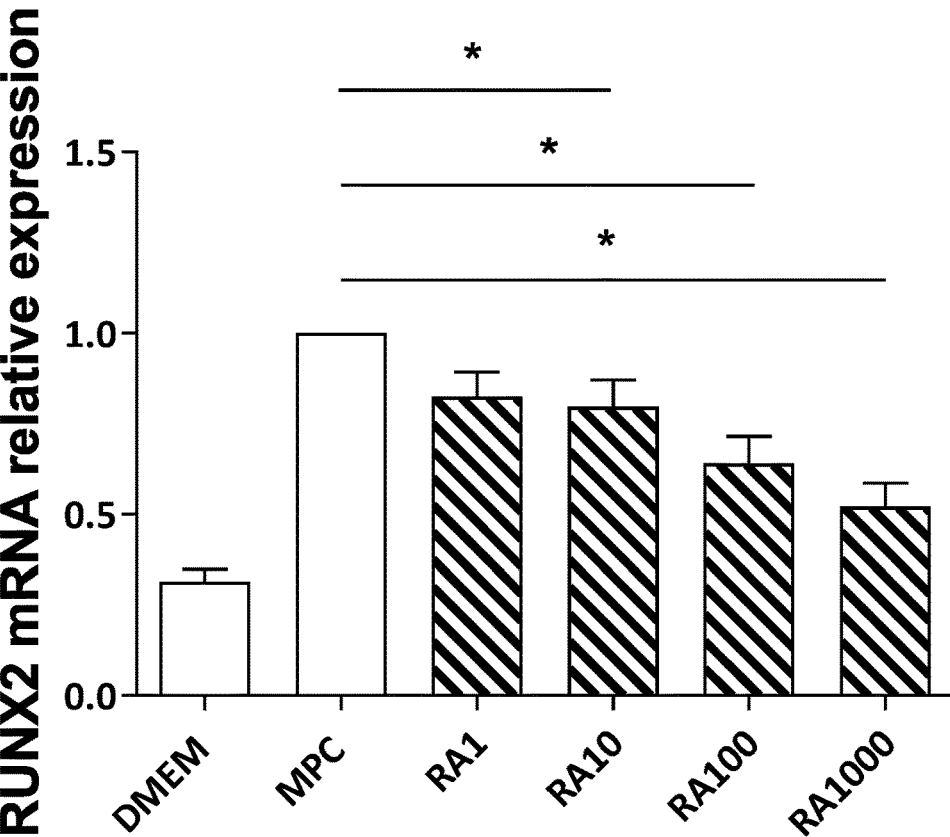

FIG. 1: Retinoic acid decreases calcification and osteoblast-like phenotype

Figure 2A:
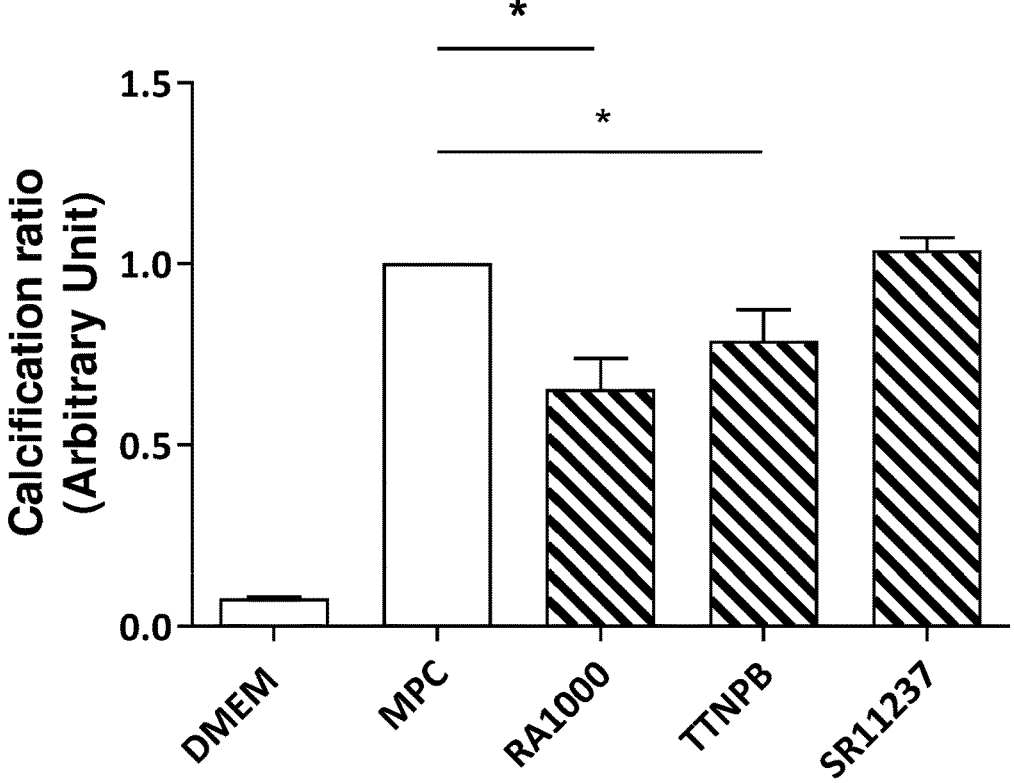
Figure 2B:
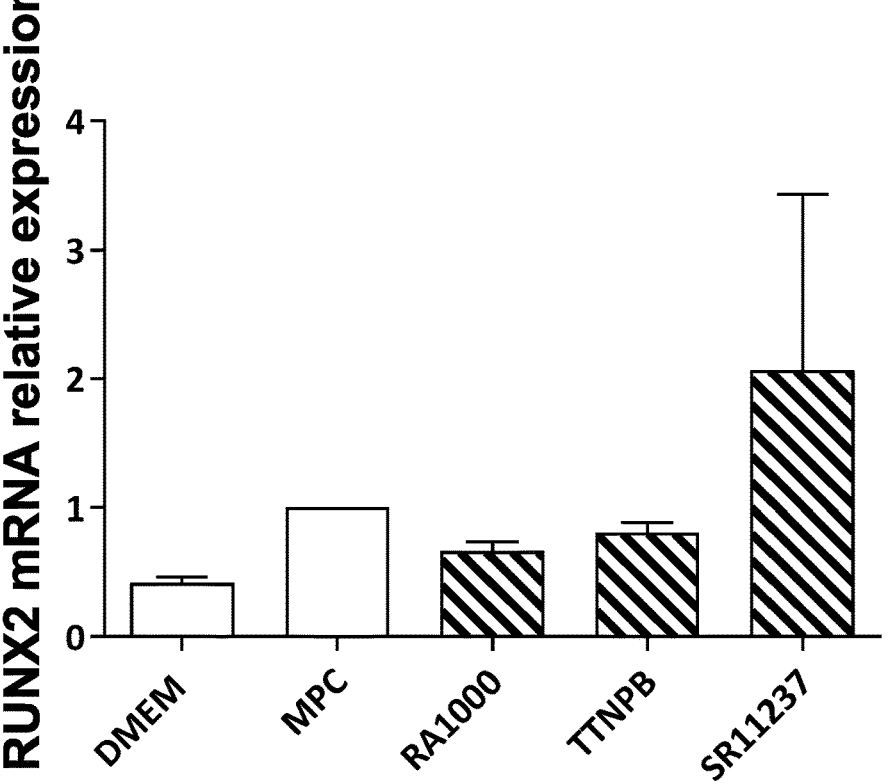
Figure 2C:
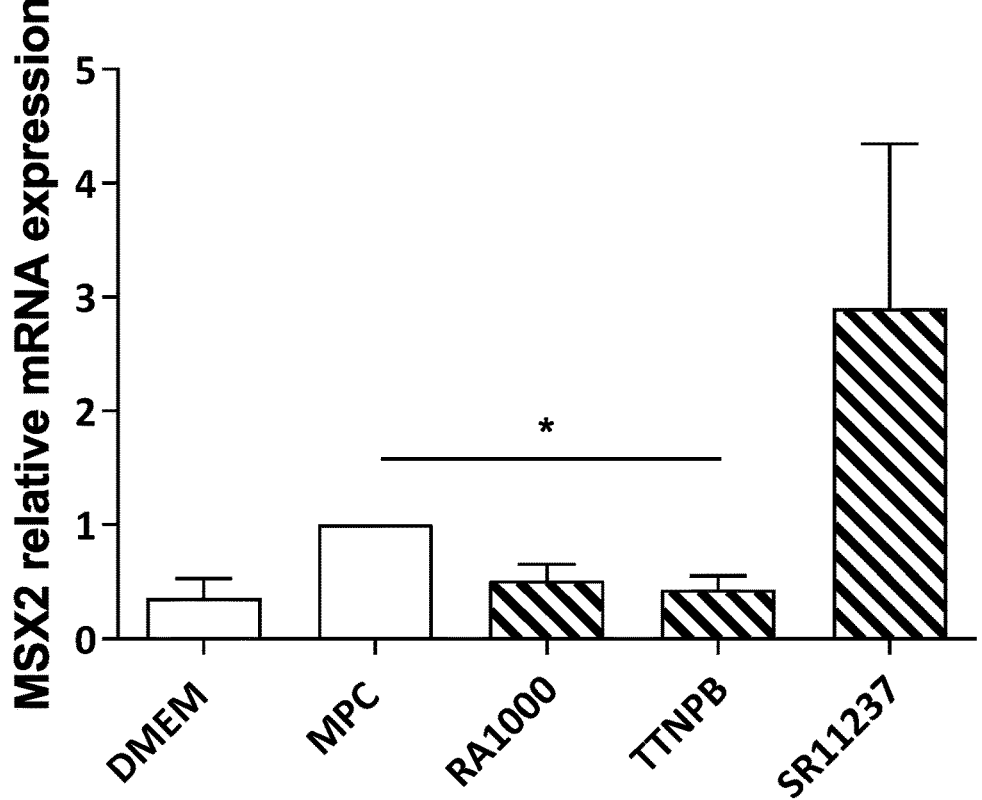
Figure 3A:
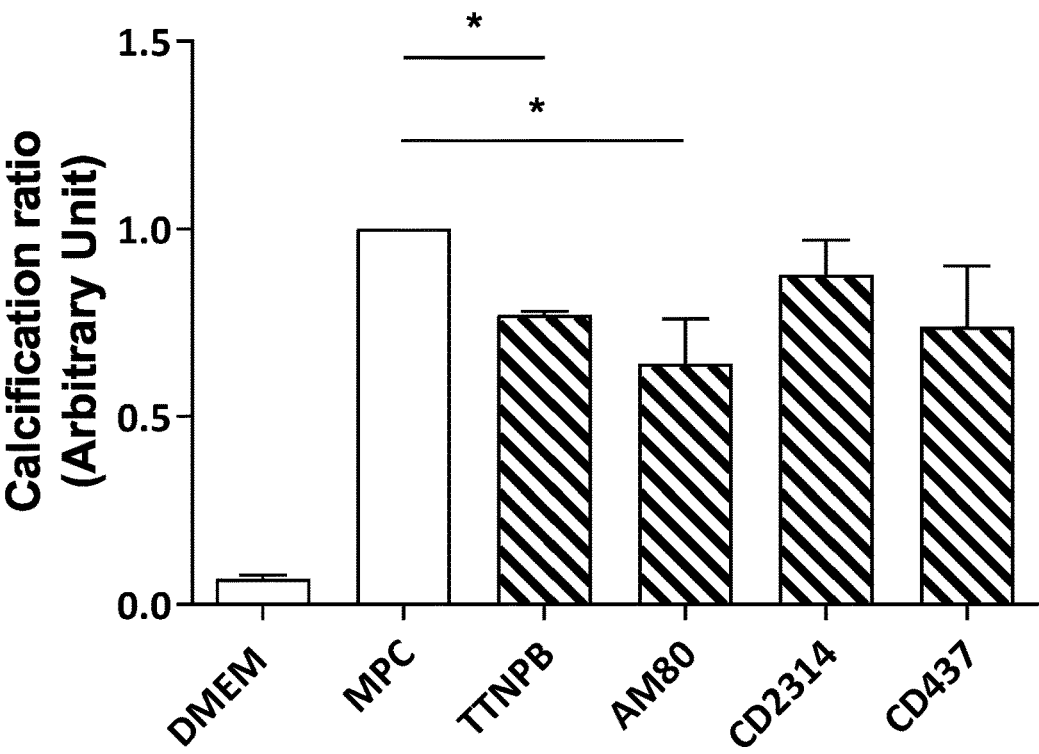
Figure 3B:
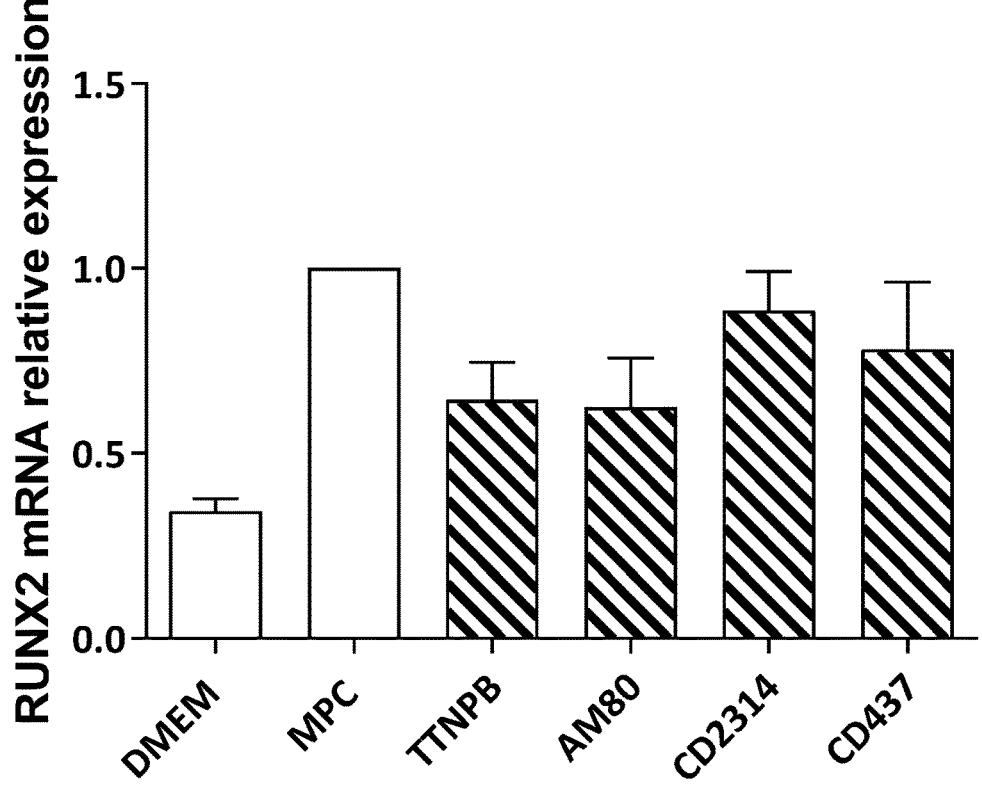
Figure 3C:
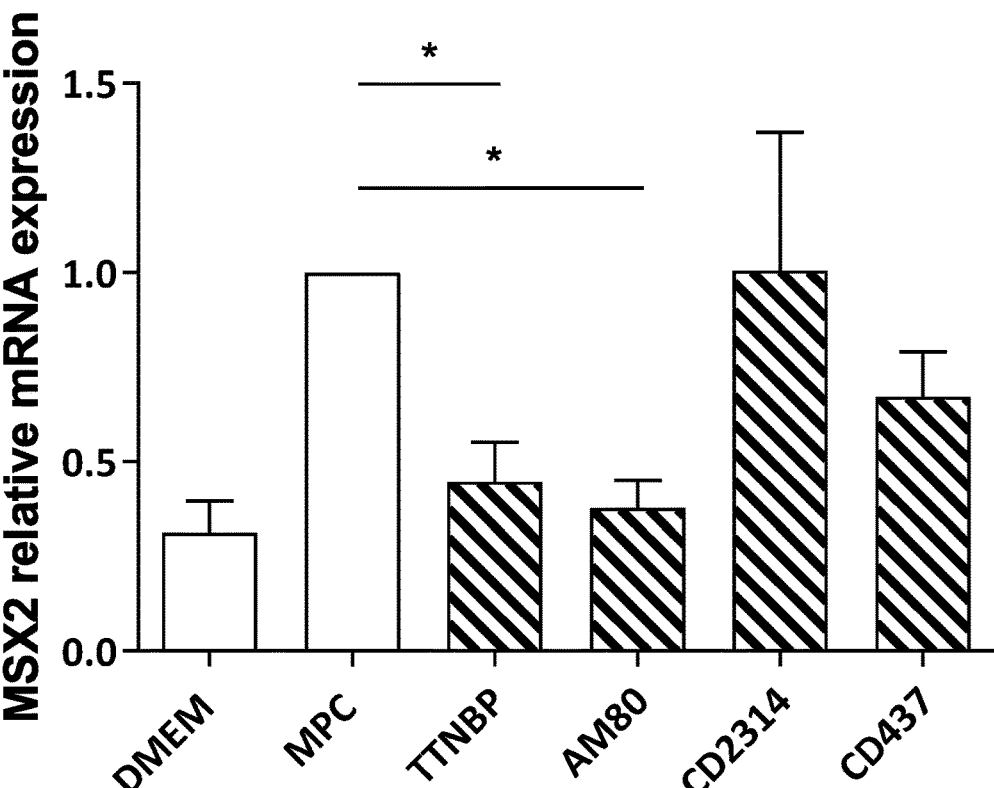
Figure 4A:
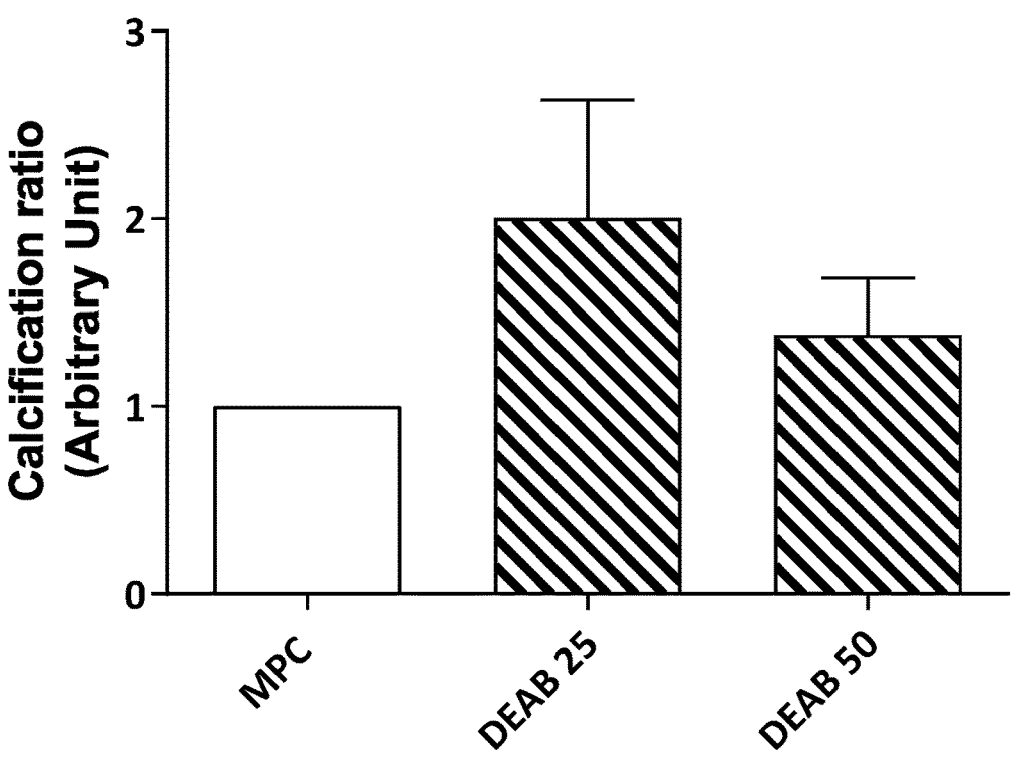
Figure 4B:
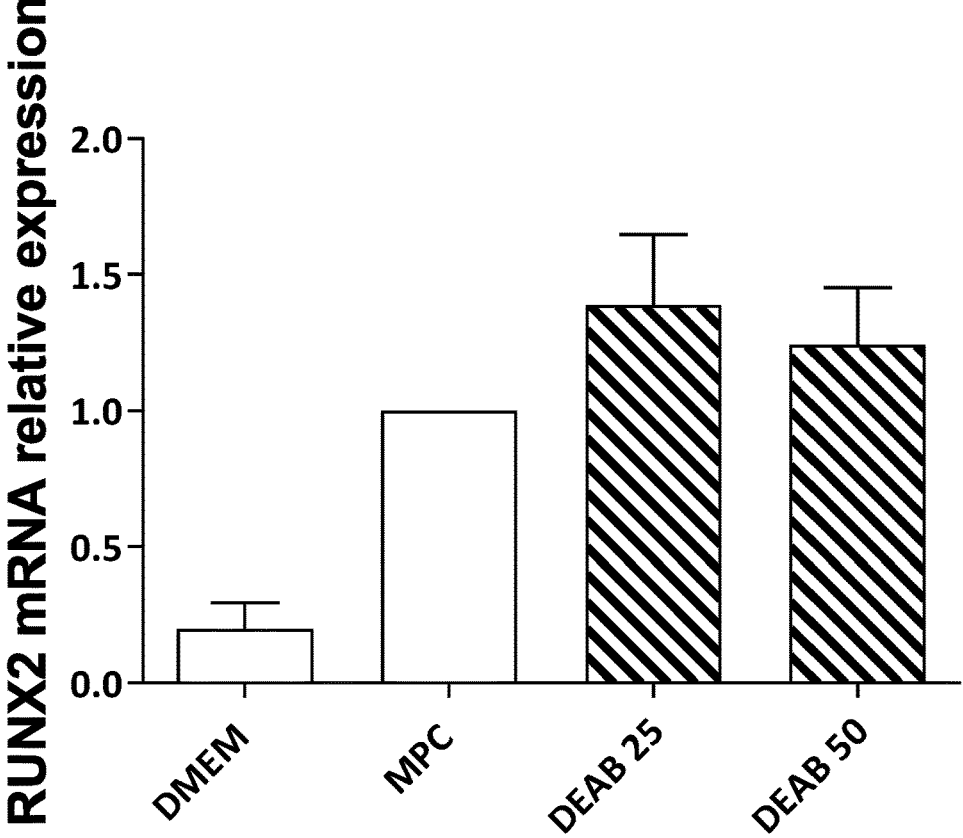

A: Calcification ratio of VIC treated with retinoic acid (1; 10; 100 or 1000 nM) in pro-calcifying medium for 7 days. Pro-calcifying medium condition is set at 1. B RUNX2 and relative mRNA expression in VIC treated with retinoic acid (1; 10; 100 or 1000 nM) in pro-calcifying medium for 7 days. Pro-calcifying medium condition is set at 1. Data are presented as mean+SEM, *: $p<0.05$ FIG. 2: Retinoids reduce calcification and osteoblast-like phenotype in a RAR activation dependent manner A: Calcification ratio of VIC treated with retinoic acid, Arotinoid acid (TTNB, RAR agonist) or SR11237 (RXR agonist) in pro-calcifying medium for 7 days. Pro-calcifying medium condition is set at 1. B and C: RUNX2 and MSX2 relative mRNA expression in VIC treated with retinoic acid, Arotinoid acid (TTNB, RAR agonist) or SR11237 (RXR agonist) in pro-calcifying medium for 7 days. Pro-calcifying medium condition is set at 1. Data are presented as mean+ SEM, *: $p<0.05$ FIG. 3: RARα activation reduces calcification and osteoblast-like phenotype in VIC A: Calcification ratio of VIC treated with Arotinoid acid (TTNB, RAR agonist), AM80 (RARα agonist), CD2314 (RARβ agonist) or CD437 (RARγ agonist) in pro-calcifying medium for 7 days. Pro-calcifying medium condition is set at 1. B and C: RUNX2 and MSX2 relative mRNA expression in VIC treated with Arotinoid acid (TTNB, RAR agonist), AM80 (RARαagonist), CD2314 (RARβ agonist) or CD437 (RARγ agonist) in pro-calcifying medium for 7 days. Pro-calcifying medium condition is set at 1. Data are presented as mean+SEM, *: $p<0.05$ FIG. 4: ALDH1A1 inhibition increases calcification and osteoblast-like phenotype in VIC A: Calcification ratio of VIC treated with 4-Diethylaminobenzaldehyde 25 or 50 nM, (DEAB, ALDH inhibitor) in pro-calcifying medium for 7 days. Pro-calcifying medium condition is set at 1. B: RUNX2 relative mRNA expression in VIC treated with DEAB in procalcifying medium for 7 days.

EXAMPLE

Methods

Modulation of Retinoic Acid Signaling in Pro-Calcifying Conditions

VIC were treated for 7 days in a medium composed of DMEM with 10% FBS, supplemented with ascorbic acid (283 µM, Sigma Aldrich), Sodium Phosphate (3 mM, Sigma Aldrich) and dexamethasone (100 nM, Stem Cell technologies). VIC were treated with retinoic acid (RA: 1; 10; 100; 1000 nM), TTNPB (RAR pan agonist, 1 µM) AM80 (RARα specific agonist, 1 µM), CD2314 (RARβ specific agonist, 1 µM), CD437 (RARγ specific agonist, 1 µM) or 4-Diethylaminobenzaldehyde (DEAB, ALDH inhibitor, 25, 50 nM).

Calcification Measurement

After 7 days of treatment, VIC were rinsed twice in PBS then fixed in paraformaldehyde 4% for 15 minutes. After washing with deionized water, calcium deposits were stained with an alizarin red solution (1%, pH 6.38) for 10 minutes. Then, cells were washed with deionized water and staining was fixed with absolute ethanol. Quantification is performed according to Gregory et al method. Briefly, cells were incubated with acetic acid 10% for 30 minutes under smooth shaking. Cells were then transferred to a microtube and vortexed for 30 seconds. Mineral oil was added to each tube and samples were heated for 10 minutes à 85° C. and cooled in ice for 5 minutes. After centrifugation (15 minutes, 16.000 g), supernatants are collected and 200 µl of ammonium hydroxide are added. Samples are then read at 405 nm in a microplate.

Quantitative PCR

RNA was extracted from VICs after homogenization in TRIzol reagent (Life Technologies), following the Chomczynski and Sacchi protocol. For gene expression analysis, 2 micrograms of total extracted RNA were reverse transcribed with the High Capacity cDNA Reverse Transcription kit (Life Technologies) in a total volume of 20 µl, according to manufacturer's procedures. Samples were incubated at 25° C. for 10 min, followed by 2 h at 37° C. The obtained cDNA were stored at −20° C. Quantitative PCR was performed using an ABI PRISM 7000 Detection System (Life Technologies). Four microliters of reverse transcription product were added to 16 µl of a mix consisting of 10 µl of master mix containing Taq polymerase, MgCl2, and dNTPs (Life Technologies), 1 µl solution containing sense and antisense primers and TaqMan® probe specific for the gene of interest and 5 µl of water. The expressions of the transcripts were normalized by Abelson (ABL) mRNA expression, used as an endogenous reference gene. The relative quantification of the transcripts was performed using the cycle threshold (Ct) comparative method and calculated with the formula $2-\Delta\Delta Ct$. For each sample, detection of PCR products was performed separately and in duplicate. ABL (Hs01104728_m1), RUNX2 (Hs00231692_m1) and MSX2 (Hs00741177_m1) commercial assays were purchased from Life Technologies.

Statistical Analyses

All data are reported as mean±SEM. A Student t-test for continuous variables were used. For all analysis, a p-value≤0.05 was considered statistically significant. All statistical analyses were performed using SPSS version 20.0 for Windows (SPSS, Inc., Chicago, Illinois).

Results

The results are depicted in FIGS. 1-4. FIGS. 1A and 1B show that retinoic acid decreases calcification and osteoblast-like phenotype. FIGS. 2A-2C show that retinoids reduce calcification and osteoblast-like phenotype in a RAR activation dependent manner. Moreover, FIGS. 3A-3C show that: RARα activation reduces calcification and osteoblast-like phenotype in VIC. Finally, FIGS. 4A and 4B show that ALDH1A1 inhibition increases calcification and osteoblast-like phenotype in VIC.

REFERENCES

Throughout this application, various references describe the state of the art to which this invention pertains. The disclosures of these references are hereby incorporated by reference into the present disclosure.

1. Nishimura R A, Otto C M, Bonow R O et al (2014) 2014 AHA/ACC guideline for the management of patients with valvular heart disease: a report of the American College of Cardiology/American Heart Association Task Force on Practice Guidelines. J Am Coll Cardiol 63(22):e57-185. doi:10.1016/j.jacc.2014.02.536
2. Yetkin E, Waltenberger J (2009) Molecular and cellular mechanisms of aortic stenosis. Int J Cardiol 135(1):4-13. doi:10.1016/j.ijcard.2009.03.108
3. Lindman B R, Clavel M A, Mathieu P et al (2016) Calcific aortic stenosis. Nat Rev Dis Primers 2:16006. doi: 10.1038/nrdp.2016.6
4. Taylor P M, Batten P, Brand N J, Thomas P S, Yacoub M H (2003) The cardiac valve interstitial cell. Int J Biochem Cell Biol 35(2):113-118
5. Liu A C, Joag V R, Gotlieb A I (2007) The emerging role of valve interstitial cell phenotypes in regulating heart valve pathobiology. Am J Pathol 171(5):1407-1418. doi: 10.2353/ajpath.2007.070251
6. Cloyd K L, El-Hamamsy I, Boonrungsiman S et al (2012) Characterization of porcine aortic valvular interstitial cell 'calcified' nodules. PLoS ONE. doi:10.1371/journal.pone.0048154

The invention claimed is:

1. A method of decreasing calcification of an aortic valve in a patient in need thereof comprising administering to the patient a therapeutically effective amount of an RARα agonist selected from the group consisting of TTNPB, tamibarotene, 9-cis-retinoic acid, trans-retinoic acid, AGN193836, and Ro 40-6055.

2. The method of claim 1 wherein the aortic valve is a diseased aortic valve.

3. The method of claim 2 wherein the patient suffers from a calcific aortic valve disease.

4. The method of claim 1 wherein the aortic valve is an implanted bioprosthetic valve.

5. The method of claim 4, wherein the step of administering prevents degeneration of the implanted bioprosthetic valve.

6. The method of claim 4 wherein the implanted bioprosthetic valve was implanted either surgically or after transcatheter aortic valve implantation (TAVI).

* * * * *